(12) United States Patent
Daniels (10) Patent No.: US 6,255,296 B1
(45) Date of Patent: Jul. 3, 2001

(54) COMPOSITION AND METHOD FOR TREATING A PATIENT SUSCEPTIBLE TO OR SUFFERING FROM A CARDIOVASCULAR DISORDER OR DISEASE

(75) Inventor: Bruce A. Daniels, Oklahoma City, OK (US)

(73) Assignee: EndoMatrix, Inc., Napa, CA (US)

( * ) Notice: Subject to any disclaimer, the term of this patent is extended or adjusted under 35 U.S.C. 154(b) by 0 days.

(21) Appl. No.: 09/302,690

(22) Filed: Apr. 30, 1999

Related U.S. Application Data (63) Continuation-in-part of application No. 08/585,743, filed on Jan. 16, 1996, now abandoned, which is a continuation of application No. 08/180,131, filed on Jan. 11, 1994, now abandoned.

(51) Int. Cl.[7] ................................................. A01N 43/04
(52) U.S. Cl. .......................... 514/56; 514/561; 514/564; 514/822; 514/824
(58) Field of Search .............................. 514/56, 561, 564, 514/822, 824

(56) References Cited

U.S. PATENT DOCUMENTS

| | | | | |
|---|---|---|---|---|
| 3,342,683 | * | 9/1967 | Hashimoto et al. | 167/74 |
| 3,574,832 | * | 4/1971 | Engel et al. | 424/183 |
| 4,404,212 | * | 9/1983 | Moncada | 424/251 |
| 5,428,070 | * | 6/1995 | Cooke et al. | 514/557 |
| 5,519,010 | * | 5/1996 | Fan et al. | 514/54 |

FOREIGN PATENT DOCUMENTS

| | | | |
|---|---|---|---|
| 57116017 | * | 7/1982 | (JP) . |
| 5163139 | * | 6/1993 | (JP) . |
| 9008784 | * | 8/1990 | (WO) . |

OTHER PUBLICATIONS

Horwiitz et al., Foundation for Vascular–Hypertension Research, 22nd annual report, pp. 9–10, 1993.*
Lewis, Hawley's Condensed Chemical Dictionary, twelfth edition, pp. 95, 590, and 591, 1993.*
Schneider, Comparison . . . in Rabbits, Arch. Pharmacol. vol. 345, Suppl 2, abstract, 1992.*
Zheng et al., Isolation . . . Panax ginseng, J. of Jilin Agricul. Univ., vol. 16, No. 4, abstract, 1994.*
Hong et al., Seasonal . . . Larix Ieptolepis, Nongdae non-munjip–thesis . . . , vol. 10, abstract, Feb. 1979.*
Takagi, Constituents . . . kombu soup stock, Nara Igaku Zasshi, vol. 24(5), abstract, 1973.*
Clark et al., Metabolism of arginine . . . mammary tissue, J. Dairy Sci., vol. 58, No. 12, abstract, Dec. 1975.*
Boshikova et al., Isolation . . . organs, Tr. Nauchnoizsled. Khim–Farm. Inst., vol. 16, abstract, 1986.*
Nader et al., Selective . . . lymphoid tissues, Biochem. Biophys. Acta, vol. 627(1), abstract, 1980.*
Kudryashov et al., Heparin . . . properties, Izv. Akad. Nauk SSSR, Ser. Biol., No. 6, abstract, 1991.*

* cited by examiner

*Primary Examiner*—Sreeni Padmanabhan
(74) *Attorney, Agent, or Firm*—Lanahan & Reilley LLP; Draper B. Gregory (57) ABSTRACT

A method for inhibiting the effects of cardiovascular disorders and diseases in a host susceptible to or suffering from a cardiovascular disorder or disease comprising administering to the host, a therapeutically effective amount of a first substance characterized as simulating a heparin-like effect, and a therapeutically effective amount of a second substance characterized as simulating an arginine-like effect; and a formulation for use in treating a host susceptible to or suffering from the effects of cardiovascular disorders and diseases comprising a therapeutically effective amount of a first substance characterized as simulating a heparin-like effect, and a second substance characterized an simulating an arginine-like effect, an described.

17 Claims, 6 Drawing Sheets

COMPOSITION AND METHOD FOR TREATING A PATIENT SUSCEPTIBLE TO OR SUFFERING FROM A CARDIOVASCULAR DISORDER OR DISEASE

This is a continuation-in part of U.S. patent application Ser. No. 08/585,743 filed on Jan. 16, 1996, now abandoned, which is a continuation of U.S. patent application Ser. No. 08/180,131 filed on Jan. 11, 1994, now abandoned.

FIELD OF THE INVENTION

This invention relates generally to a method and formulation for treating a patient susceptible to or suffering from cardiovascular disorder or disease, and more particularly, but not by way of imitation, to a method and formulation for preventing and treating atherosclerosis, arteriosclerosis, congestive heart failure, arterial stenosis, re-stenosis, re-stenosis, smooth muscle cell hydro trophy, cardiac cell hydro trophy, thrombogenicity, clotting disorders, platelet disorders, myocardial infarction, cerebrovascular ischemic, peripheral vascular ischemic, angina pectoris or hypertension.

BACKGROUND OF THE INVENTION

Cardiovascular disorders and diseases, and their associated complications are a principal cause of disabilities and deaths of individuals in the United States and Western Europe. For example, in recent years more than 500,000 deaths have occurred annually in the United States alone as a result of coronary artery disease, and an additional 700,000 patients have been hospitalized for myocardial infarction.

There has been an ongoing search for effective long term treatment for disorders and diseases of the heart and arteries, such as atherosclerosis, arteriosclerosis, congestive heart failure angina pectoris, and other disorders and diseases associated with the cardiovascular system. Prior treatments for such disorders or diseases include administration of vasodilators, angioplasty and by-pass surgery, for example. Such treatments have met with great disapproval due to the risks versus the benefits gained by the various treatments. Such treatments have serious shortcomings in long term effectiveness. The use of vasodilators drugs and mechanical treatments for acute and chronic occlusive vascular diseases of the heart, central, and peripheral vascular system have to date been ineffective for favorable long term results. The outcome with current treatments is minimally impacted because the treatments are directed toward the effects of the underlying disease process rather than the initial molecular cause of the disease or disorder.

For example, the rationale for vasoactive drugs is to reduce blood pressure by acting directly or indirectly on vascular, and/or cardiac, smooth muscle and thereby decreasing vascular resistance and abnormalities to flow. Such drugs do not treat the initial cause of elevated pressure and abnormal flow. Rather, they seek to reduce the resulting effect of the disease or disorder. Such drugs activate the sympathetic nervous system by way of the baroreceptor reflex to produce an increased heart rate and force of myocardial contraction which are not beneficial effects. Other side effects from such drugs include headache, heart palpitations, anxiety, mild depression, dry-mouth, unpleasant taste in the mouth, nausea, vomiting, angina, myocardial infarction, congestive heart failure, decreased cardiac output, fluid retention, fatigue, weakness and others. Pharmacological treatment of most diseases is not very specific in its effect on the initial molecular cause of the disease activity, and treats a very limited spectrum of effects in diseases which are multifactorial.

As a further example, such improved outcome in atherosclerotic vascular diseases is seen with cholesterol reduction and drug treatment for lipid disorders. However, these treatments do not treat the clotting abnormalities associated with these disease states which are known to be the proximate event causing heart attack and stroke. These do not prevent the cellular or molecular reactions attributed to platelets, macrophages, neutrophils, lymphocytes, smooth muscle cells, and other cell types known to be involved in atherosclerosis and complications of the disease.

Likewise, thrombolytic therapy, angioplasty and by-pass surgery have been minimally successful long term. Current mechanical and pharmacological treatments focus on a particular partial or complete occlusion or occluded vessel where, at the particular site, it is either unclogged or by-passed with connecting vessels. These treatments fail to address the physiologic derangements of normally homeostatic systems which allow the occlusive process to begin and progress. Likewise, they fail to address the multicentric nature of the homeostatic derangements. These failures frequently result in recurrent occlusion in the initially treated vessel, microembolism from incomplete resolution of thrombus at the occlusive site treated, and no treatment for sites not judged to be adequately occluded or stenotic by currently available, crude technologic methods.

There remains a great need for treatment which prevents the failure of the normal homeostatic controls and which restores these controls once derangements begin to develop. Restoration of the endogenous regulatory systems and cellular domains to a healthy state could prevent the stenosis, occlusion, thrombosis, and thromboembolic processes which occur as a consequence of such derangements. Continuous and episodic restoration of control in the normal molecular processes which finely regulate homeostasis can prevent atherosclerosis, variants thereof, hypertension, congestive heart failure, macro and micro-thrombosis and thromboembolism, and complications of these disease processes, including, but not limited to, myocardial infarction, cerebrovascular accident, related kidney diseases, related central and peripheral nervous system disorders, and related diseases in other cellular systems. In addition, rapid restoration of homeostatic control once injurious processes accelerate and accumulate can minimize both the extent of and duration of consequences on atomic, molecular, membrane, cellular, and organ levels.

SUMMARY OF THE INVENTION

It is the conception of the inventor that the cellular matrix composed of heparin-arginine-water polymers is responsible for the controlled molecular milieu comprising the cellular environment. It is these polymers which determine the protein distribution, functionality, DNA-RNA transcription regulation, and the physical properties of cells.

These polymers create the regulated, homeostatic control in physiologic systems; they are ubiquitously present throughout cellular domains and as such are responsible for the possibilities of molecular reactions of various types.

The normal cellular processes associated with life lead to re-arrangement, altered binding, destruction and change of these polymers. The changes within the polymers lead to changes in protein binding, protein interactions, and transcriptional processes.

The nature of these changes and their locations lead to altered molecular reactions of a non-homeostatic nature which eventuate in processes ultimately recognized as diseases. Where the polymer changes occur in the cellular environments, and the magnitude of these changes determines what type of disease develops.

It is an object of the present invention to provide a treatment which is directed to preventing and minimizing dysfunctional atomic and molecular interactions within human cellular environments and membranes which lead to atherosclerosis and other vascular diseases in which endothelial cells'components and molecules modulate molecular reactions by coadministration of exogenous sources of heparin and arginine and functional analogs or physiologically acceptable salts thereof.

It is another object of the present invention to provide a treatment which is directed to retarding adverse consequences of free radicals generated in human cellular domains by coadministration of exogenous sources of heparin and arginine and functional analogs or physiologically acceptable salts thereof.

It is a further object of the present invention to create an enhanced state of homeostasis within human cellular environments and membranes by coadministration of exogenous sources of heparin and arginine and functional analogs or physiologically acceptable salts thereof.

It is still a further object of the present invention to trigger an auto-regulated endogenous heparin production cycle within human cellular environments and membranes by coadministration of exogenous sources of heparin and arginine and functional analogs or physiological acceptable salts thereof.

It is another object of the present invention to stimulate an increased production of nitric oxide and prostacyclin within human cellular environments and membranes by coadministration of exogenous sources of heparin and arginine and functional analogs or physiologically acceptable salts thereof to produce a synergistic effect.

It is a further object of the present invention to provide a treatment which is directed to preventing and minimizing non-homeostatic atomic and molecular interactions within human cellular environments and membranes which lead to congestive heart failure and disorders and complications thereof by coadministration of exogenous sources of heparin and arginine or functional analogs or physiologically acceptable salts thereof.

It is still another object of the present invention to provide a treatment which is directed to preventing and minimizing non-homeostatic levels of atomic and molecular interactions within human cellular environments and membranes which lead to angina pectoris, coronary artery disease, re-stenosis following mechanical and pharmacological treatments of stenosis, peripheral vascular disease, ALS, lupus and to disorders and complications thereof by coadministration of exogenous sources of heparin and arginine and functional analogs or physiologically acceptable salts thereof.

It is still a further object of the present invention to provide a treatment which is directed to restoring cellular homeostatic processes and repairing membranes and tissues to alleviate the conditions associated the atherosclerosis, such as free radical injury, infarction, hypertrophy, hypertension, cell migration, activation, and transformation, cytokine injury, thrombotic states, and vascular and tissue ischemic states by coadministration of exogenous sources of heparin and arginine and functional analogs or physiologically acceptable salts thereof.

It is another object of the present invention to provide a treatment which is directed to the retarding of the aging process by coadministration of exogenous sources of heparin and arginine and functional analogs or physiologically acceptable salts thereof.

It is yet a further object of the present invention to provide a treatment which is directed to the repairing of cellular membrane and processes to promote accelerated wound healing by coadministration of exogenous sources of heparin and arginine and functional analogs or physiological acceptable salts thereof.

It is still another object of the present invention to provide a treatment which is directed to the repairing of cellular membrane and processes to prevent malignancies and effectively cause regression, stabilization, control and prevention of malignancies and/or metastases from malignancies by coadministration of exogenous sources of heparin and arginine and functional analogs or physiologically acceptable salts thereof.

It is still a further object of the present invention to provide a treatment which is directed to decreasing thrombogenicity and repairing cellular processes and improving blood rheologic properties that are associated with thrombosis and hypoxia within a human cellular environment by coadministration of exogenous sources of heparin and arginine and functional analogs or physiologically acceptable salts thereof.

It is an object of the present invention to avoid known side effects such as thrombocytopenia and bleeding attendant with the administration of heparin alone by coadministration of heparin and arginine.

It is an object of the present invention that the co-administration of heparin and arginine by various routes, including the oral route of co-administration, is recognized herein to minimize any tendency for hemorrhagic complication, thrombocytopenia, allergic reaction, and adverse drug interaction. In fact, it is believed that said oral co-administration has effects which amplify the homeostatic properties inherent in both heparin and arginine functionalities.

Lastly, it is an object of the present invention to provide a treatment for diseases related to the immune system by repairing and maintaining the dominant cellular homeostatic processes within a human cellular environment through coadministration of exogenous sources of heparin and arginine and analogs or physiologically acceptable salts thereof.

Accordingly, an embodiment of the present invention is directed to a method of treating a patient susceptible to or suffering from a cardiovascular disorder or disease comprising the steps of coadministering a composition including a therapeutically effective amount of a first substance having a heparin-like effect to the patient and a therapeutically effective amount of a second substance having an arginine-like effect to the patient. Additionally, the substances may be dispersed in a physiological, non-toxic vehicle, such as water. The coadministration of these substances includes one of intravenous, subcutaneous, oral, transdermal and intrapulmonary administration.

Another embodiment is directed to a composition for treating cellular membrane and environments within a patient susceptible to or suffering from a cardiovascular disorder or disease, comprising of a therapeutically effective amount of exogenous heparin, analogs and functional equivalents thereof or physiologically acceptable salts thereof which enhance and induce homeostasis within endogenous human cellular membranes and environments and a therapeutically effective amount of exogenous arginine, analogs or functional equivalents or physiologically acceptable salts thereof which enhance and induce homeostasis within endogenous human cellular membranes and environments, which said amounts are effective to therapeutically treat the cellular membranes and environments.

Further provided is an article of manufacture comprising of packaging material of a pharmaceutical agent contained within said packaging material, wherein the pharmaceutical agent is therapeutically effective for treating the cellular membranes and environments within a patient having conditions associated with at least one of atherosclerosis, congestive heart failure, stroke, arterial stenosis, re-stenosis, hypertension, smooth muscle cell and cardiac muscle cell hypertrophy, thrombogenicity, clotting and platelet disorders, HIV and other infections, myocardial infarction, cerebrovascular and peripheral vascular ischemia, amyotrophic lateral sclerosis, multiple sclerosis, neurologic diseases, memory loss, inflammatory diseases, diabetes, emphysema, pulmonary fibrosis, cancerous and precancerous conditions within the cellular membrane and environment of a human, wherein the packaging material comprises a label which indicates that the pharmaceutical agent can be used for conditions associated with at least one of atherosclerosis, arteriosclerosis, states of hypoxia in cellular environment, congestive heart failure, arterial stenosis, re-stenosis, hypertension, smooth muscle cell and cardiac muscle cell hypertrophy, various hypertrophic organ diseases including prostatic hypertrophy, thrombogenicity, clotting and platelet disorders, HIV and other infections, Lupus, and other immune disorders, asthma, myocardial infarction, cerebrovascular and peripheral vascular ischemia and infarction, amyotrophic lateral sclerosis, multiple sclerosis, diabetes and its complications, emphysema, pulmonary fibrosis, cancerous and precancerous conditions, and wherein said pharmaceutical agent comprises a composition including a therapeutically effective amount of exogenous heparin or functional equivalents or physiologically acceptable salts thereof and a therapeutically effective amount of exogenous arginine or functional equivalents or physiologically acceptable salts thereof which enhance and induce homeostasis within endogenous human cellular membranes and environments.

The therapeutically effective amount of the heparin-like activity is defined primarily by the clinical response and ranges from 2,000 to 200,000 units daily, on variable schedule. For example, the heparin is characterized such that it should be an amount sufficient to exert antithrombotic effects and less than an amount to cause serious hemorrhaging while effectively maintaining the integrity and functionality of the cellular membranes and surrounding environments. The therapeutically effective amount of the arginine-like substance ranges from 500 to 50,000 mg daily dependent on the underlying condition and nature of the physiological and processes requiring treatment. For example, the arginine should be a sufficient amount to sustain a level of nitric-oxide to keep various cell types from dysfunctional activation states in the patient, to increase prostacyclin secretion, to reduce secretion of extracellular proteins and heparin binding proteins, to bind to available sulfate and carboxyl groups on heparin to increase the extracellular matrix barrier properties by decreasing the extracellular matrix pore size and permeability which in turn has a favorable effect on rheologic flow mechanics and prevent non-homeostatic interactions of various molecules with heparin and its constituent components.

The present invention is directed to a method and a formulation for inhibiting cardiovascular disorder or disease in a patient susceptible to or suffering said cardiovascular disorder or disease. In accordance with the invention, a patient susceptible to or suffering from a cardiovascular disorder or disease such as atherosclerosis, arteriosclerosis, congestive heart failure, arterial stenosis, re-stenosis, smooth muscle cell hydro trophy, cardiac cell hydrotrophy, thrombogenicity, clotting disorders, platelet disorders, myocardial infarction, cerebrovascular ischemic, peripheral vascular ischemic, angina pectoris or hypertension, is treated with a therapeutically effective amount of a first substance characterized as simulating a heparin-like effect, and a second substance characterized as simulating an arginine-like effect.

DETAILED DESCRIPTION OF THE PREFERRED EMBODIMENT

The drawings of the present invention aid to illustrate what are believed to be key heparin polymers and processes which pertain to the treatment, regulation and repair of extracellular and cellular environments and processes within a human having one or more of atherosclerosis, congestive heart failure, stroke, arterial stenosis, re-stenosis, hypertension, smooth muscle cell and cardiac muscle cell hypertrophy, thrombogenicity, clotting and platelet disorders, HIV and other infections, myocardial infarction, cerebrovascular and peripheral vascular ischemia, amyotrophic lateral sclerosis, multiple sclerosis, diabetes, emphysema, pulmonary fibrosis, lupus, ALS, cancerous and precancerous conditions. An efficiently operating homeostatic system is crucial to cellular function within mammalian organisms. In a healthy state, there is formed a gel matrix of heparin, arginine and water polymers, which houses a plurality of other molecules by accommodating dynamic binding of and release of such molecules without reaching concentration levels which destroy the gel structure and its regulatory functionalities.

Figure 1:
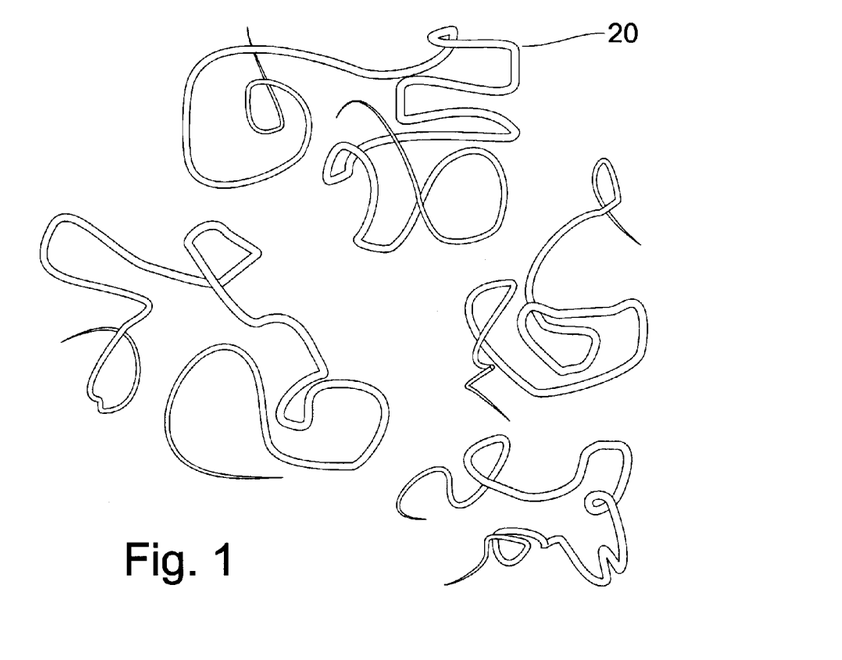
FIG. 1 is a representation of long-chain heparin polymer.
Figure 2:
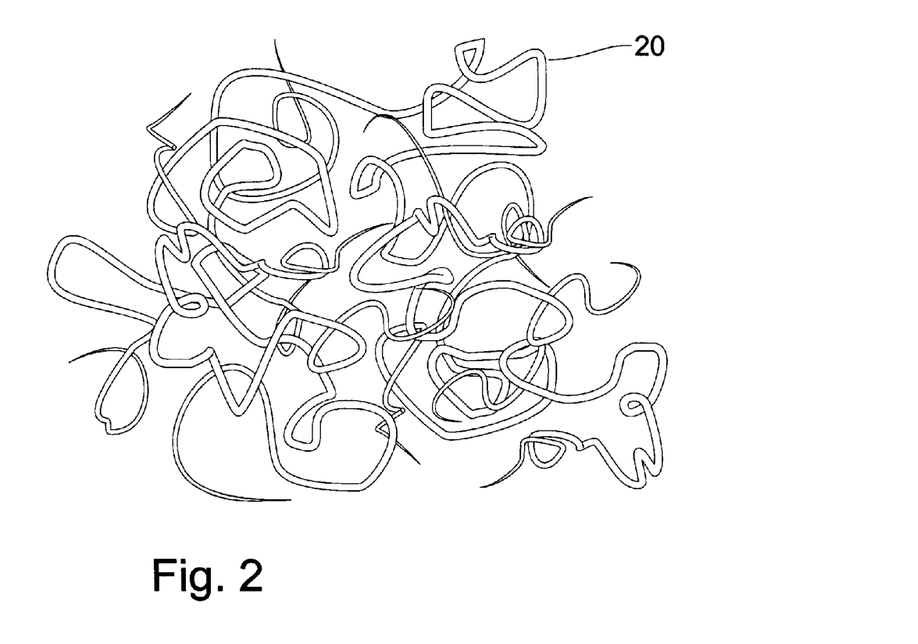
FIG. 2 is a representation of densified higher polymer.
Figure 3:
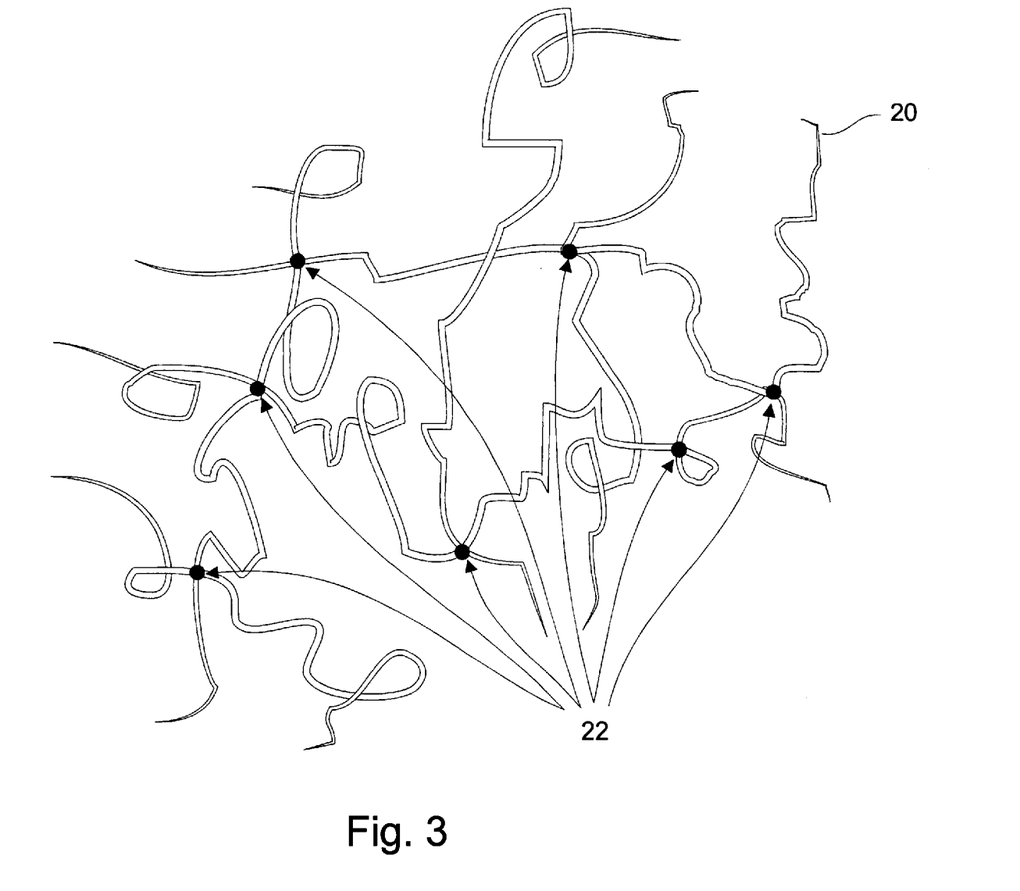
FIG. 3 is a representation of arginine cross-linking heparin polymers, wherein heparin has self-association and association with water.

FIG. 1 is a representation of long-chain heparin polymer 20 and FIG. 2 represents the polymer 20 in a densified form. FIG. 3 is a representation of arginine 22 cross-linking heparin polymers 20 to form a matrix.

Figure 9:
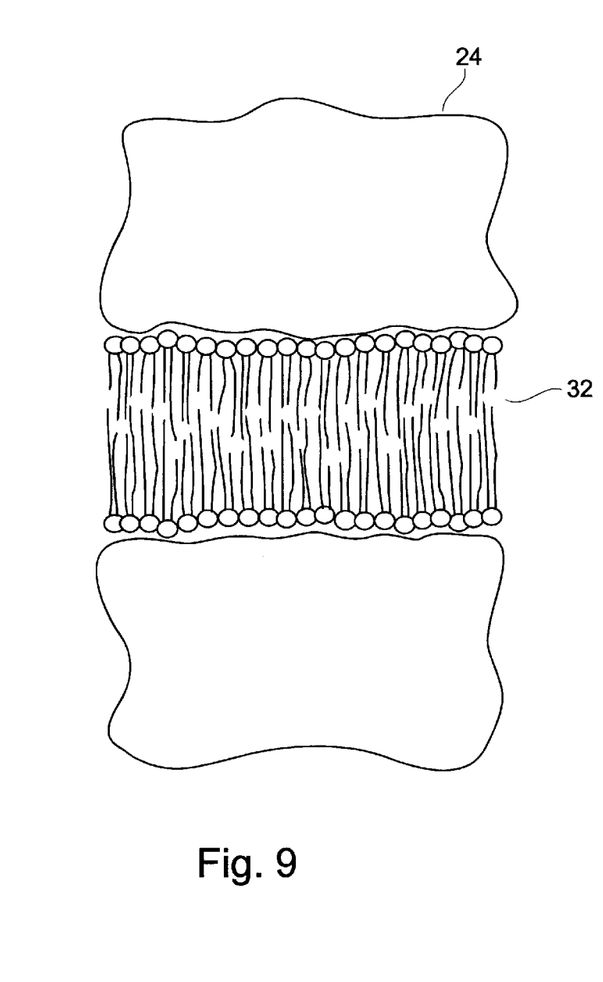
FIG. 9 is a representation of bilipid layer held between two bodies of heparin-arginine-water gel.

Polymer strands 20 are an organizing determinant for membranes, proteins, receptors, ion channels, cell organelles, nuclear membranes, membrane pores, and other complex cellular constituents. The polymers 20 and 22 organize water into arenas for confining bilipid layer membranes 32, for example, creating cell turgor and form and limiting hydrolytic properties of water on other molecular structures, as shown in FIG. 9. Without their organization, cells could not organize into confined arenas of molecular reactions with consistent functionality.

Heparin's 20 high sulfate content imparts a high negative charge which attracts and binds positively charged substances like basic amino acids, basic domains of proteins and peptides, cations, water and other such charged molecules. Arginine 22 has a high positive charge and strongly associates with heparin along membrane surfaces such as endothelium and basement membranes and in association with water 26, organize as gel matrix 24.

The gel may be in a constant state of change including transitions from one state or phase to another. As such, the conformation can change and derangements occur as different substances move in and out of the gel and as the gel properties change.

Figure 4:
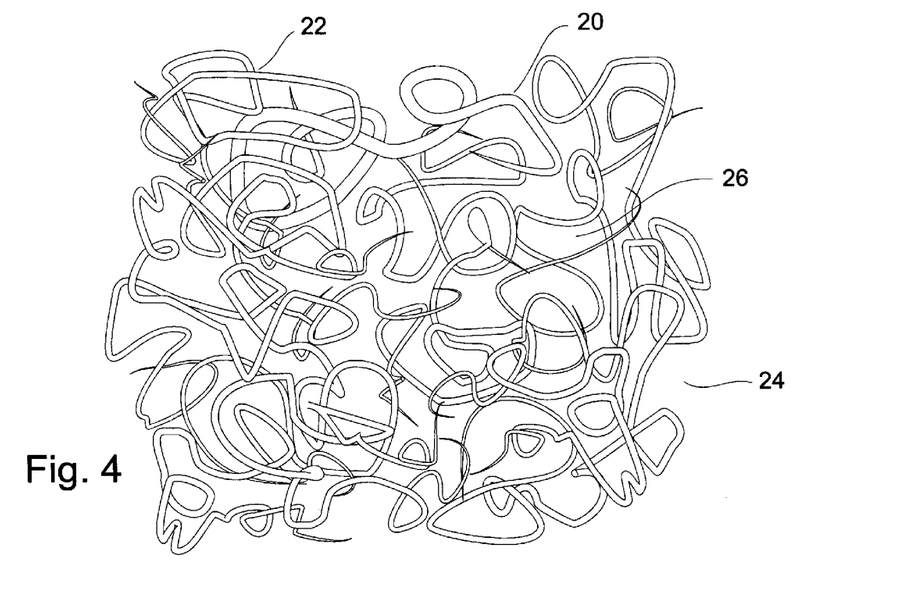
FIG. 4 is representation of a healthy gel matrix composed of multiple polymers.
Figure 5:
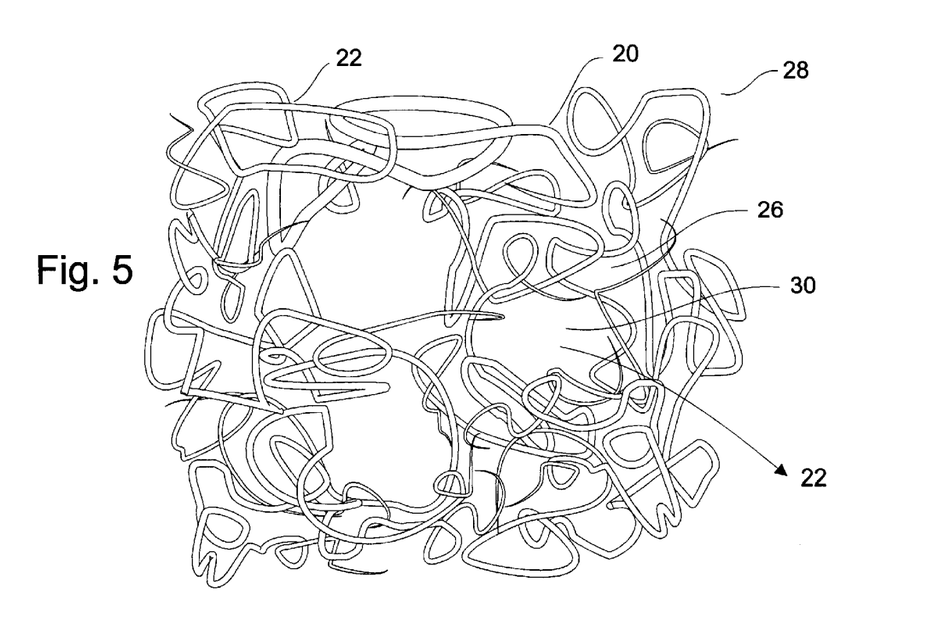
FIG. 5 is a representation of holes created by bonding of clotting factors and lipoproteins onto binding sites precluding cross-linkage of polymers strands and self-association of strands.
Figure 6:
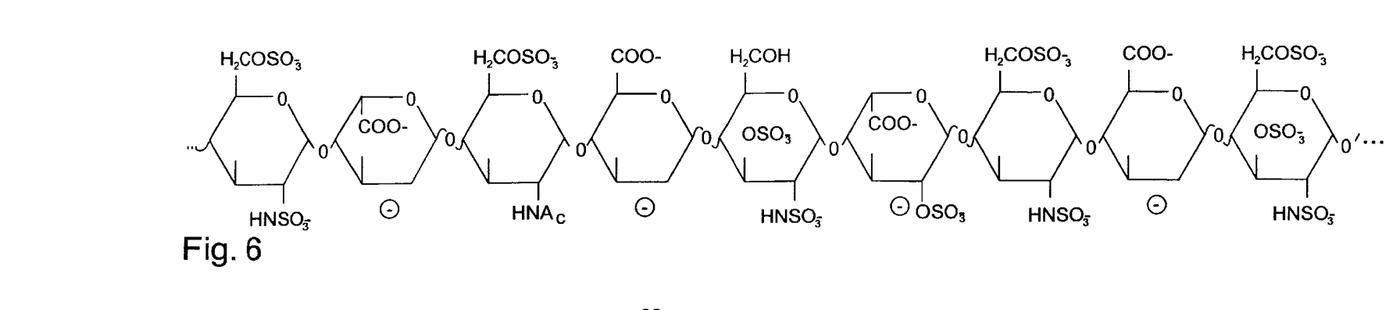
FIG. 6 is a representation of a chemical structure of a heparin polymer.
Figure 7:
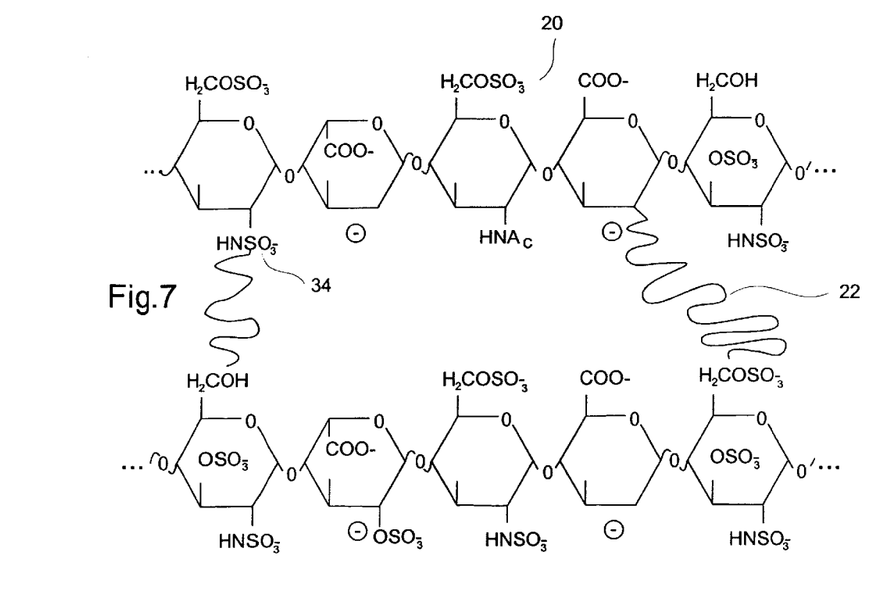
FIG. 7 is a representation of a chemical structure of a heparin-arginine-heparin cross-linked polymer.
Figure 8:
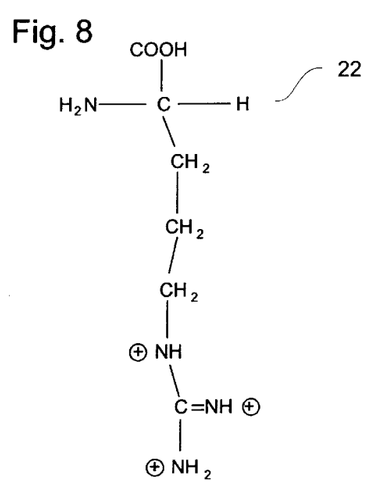
FIG. 8 is a representation of chemical arginine structure.

A healthy gel matrix 24, as shown in FIG. 4, is formed from endogenous heparin 20, endogenous arginine 22 and water 26. FIG. 5 depicts an unhealthy state of a gel matrix 28 wherein some of the arginine molecules 22 have been cleaved out of the gel 28. Likewise, heparin 20 has been removed from the gel 28. There are created gaps 30 into which other molecules can embed and through which they can pass. As seen in FIGS. 6–8, a representative chemical structure of heparin polymer 20, heparin 20-arginine polymer 22 and arginine polymer 22 are shown, respectively. Arginine groups 22 are attached to the sulfate sites 34 along the polymer 20, wherein the $NH_x$ (e.g. x=1 or 2) groups are positively charged and attach to negatively charged $SO_3$ groups. A higher number of cross linking bonds which exist between heparin 20 equates to a higher densification characteristic of the gel matrix with smaller pores.

The healthy gel structure 24 has a conformation that preferentially supports interaction and binding of foreign molecules. The capacity to accommodate intrusions of such molecules before the gel structure collapses and loses its functionality is an important characteristic of the gel system.

An example of polar molecules that heparin binds and inactivates thereby modulating their activity, are serine proteases, other clotting factors and thrombolytic agents, antithrombin-thrombin, complement, apo-lipoproteins, growth promoting factors, mitogens, heparinase, lipoprotein lipase, growth inhibiting factors, chemotactic factors, super oxide dismutase, cytokines, numerous enzymes, and cytoskeletal proteins such as fibronectin.

As these intrusions accumulate locally or in a distributed fashion, they cause an interference within the gellular association of heparin 20 and arginine 22. The interference can cause the gel structure to deteriorate increasing its porosity or collapse altogether in a localized or distributed fashion. In addition, the intrusion may trigger a release of other bound polar molecules, such as calcium to induce a non-homeostatic event.

Figure 10:
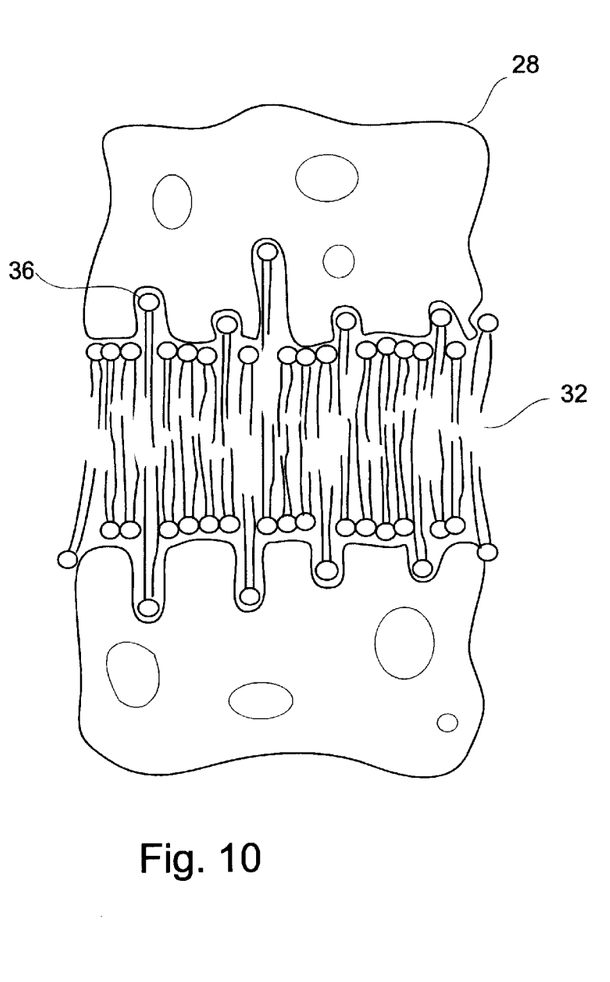
FIG. 10 is a representation of a disrupted bilipid layer, wherein the gel matrix has holes with straying phospholipid molecules therein.
Figure 11:
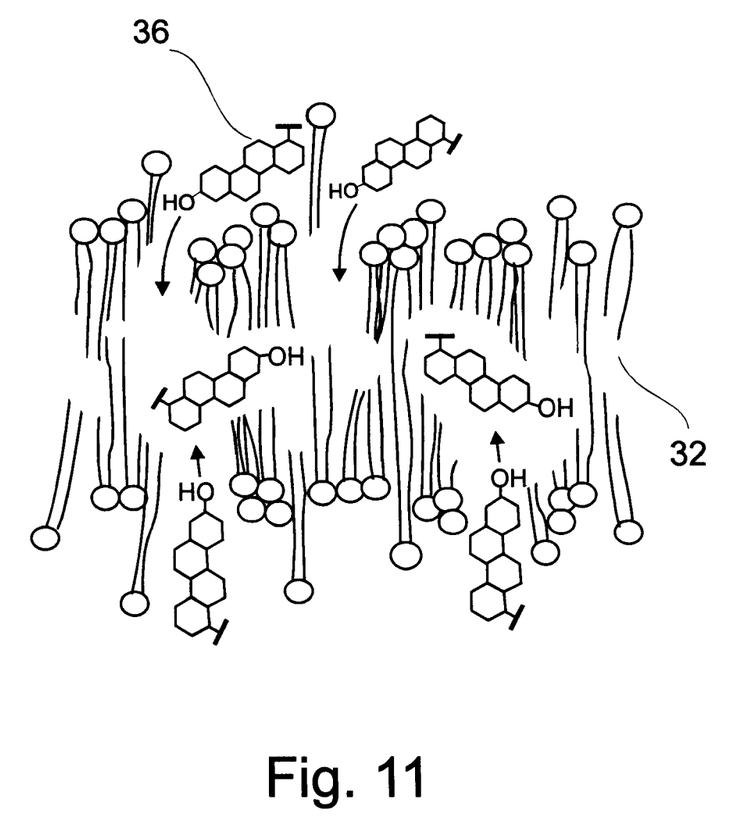
FIG. 11 is a representation of polar plaque forming molecules entering the bilipid layer through openings formed in the heparin-arginine-water gel.

The permeability created by the interference of such molecules allows macromolecules or cells 36 to enter and traverse the gel 28, as shown in FIG. 10. For example, cholesterol, clotting factors and water traverse the gel reaching a bilipid layer, or other subendothelial locations, as seen in FIG. 11. In addition, ionic strength, flow stress, heat, osmotic pressure or other forms of energy transfer to the gel can deteriorate the properties of the gel as described above.

These intrusions result in a displacement of arginine and increased generation of nitric oxide as an additional effect. Intrusions limit the binding capacity of the heparin for arginine and other molecules within the gel.

In order to reverse this disruption of the gel matrix caused by removal of arginine and/or heparin, the present invention employs a composition and treatment to maintain and rejuvenate the gel matrix and its functionality. In this regard, the present invention utilizes a full range of molecular weight heparin and arginine to give optimal pore closure and stabilization, and number and distribution of binding sites, wherein signaling, antiproliferation, antithrombotic, anticoagulant properties are maintained. Thus, it is envisioned that the homeostasis promoting functionalities of heparin, arginine, and heparin-arginine-water gel matrix, resultant from the herein described treatment, retard continuous and accumulative injury to cellular domains. By this retarding effect, cholesterol accumulations, generally referred to as "arterial plaques" are minimized. It is specifically recognized that a result of the reversibility of these injurious processes, by the currently described treatment is regression of such plaques. Attendant to this regression is decreased clotting factor activity on both a microscopic and macroscopic scale. Hence, the recognized effects of the treatment in prevention of thrombus formation, microemboli, and plaque rupture with resultant acute thrombotic occlusion.

It is also specifically recognized that heparin and arginine co-administration leads to increased Lipoprotein Lipase release with beneficial effects on plaque stability, growth, rupture, and regression. Additionally, the increased nitric oxide activity occurring with arginine administration enhances plaque regression and intimal thickening regression.

It is believed that the expression of endogenous heparin is surface receptor dependent in that prostacyclin in association with heparin at the gel surface generates a signal to the golgi apparatus to produce endogenous heparin. Added exogenous heparin accumulates at the blood/endothelium surface thereby reconstituting the prostacyclin receptors which may have been damaged and depleted over time. Nitric oxide production at or near the same surface occurs from nitric oxide synthase action on exogenous and endogenous arginine substrate. This nitric oxide amplifies the signal by increasing the local concentration of prostacyclin, whose production is mediated by the nitric oxide.

Thus, heparin is generated in quantities sufficient to allow reassociation of arginine and heparin and restore the gel structure and releases or rearranges potentially injurious molecules in the gel matrix.

The addition of heparin to the gel system protects the functionality of the arginine in the gel and the addition of arginine to the gel system protects the functionality of heparin in the gel. In the extragellular medium, the ability of heparin to bind and quiesce molecules is augmented by the simultaneous addition of exogenous heparin and exogenous arginine, wherein exogenous heparin is binding to extragellular potentially intruding molecules and allowing existing gellular heparin to associate with gellular arginine. Exogenous arginine becomes the more available substrate for nitric oxide synthase, thereby protecting gellular endogenous arginine from the nitric oxide synthase activity and allowing the endogenous arginine to continuously re-associate with the gellular heparin protecting the gel functionality.

Nitric oxide produced from arginine is an important physiological mediator. The enzyme responsible for nitric oxide production, nitric oxide synthase, requires $Ca^{++}$, Calmodulin and other co-factors. The functionality of heparin-arginine gel includes its binding and regulation of $CA^{++}$, Calmodulin and co-factors. By regulating Calmodulin activity, the heparin-arginine gel regulates nitric oxide synthase activity responsible for nitric oxide production. Anti-clotting, clotting and thrombolytic molecules and other Calmodulin mediated enzyme activations are regulated similarly by the gel.

It is believed that binding of water, small anions and cations within the heparin-arginine-water gel is facilitated by pi-bonding properties inherent in the saccharide ring structure within the heparin polymers. Changes in the shared electron density and electrical charge variation regulate the state of solvation and conformation of the gel polymers. Thus, small anion and cation binding induces changes in the state of solvation, thus, changes in catalytic and hydrolytic properties of water, and capacity of the gel to bind water and other molecules.

The following agents are believed to cause cellular damage by unfavorable interaction with the gel matrix: clotting factors hyaluronic acid, protein antibodies, hypoxemia, epinephrine, norepinephrine, anions and cations, hypertonic glucose, hyper molar solutions, insulin, angiotensin, endothelin, tumor necrosis factor, free radicals, apo-lipo proteins, thromboxane, iron, various phosphorylated molecules and agents, phospholipids, including platelet activating factor, protamine, histamine, complement, various proteolytic enzymes, various cytokines, platelet derived growth factor, various endoglycosidases, various growth factors, collagen, triglycerides, viral proteins, bacterial antigens, some prostaglandins, flow stress, fibronectin, macrophages, neutrophils, other leukocytes, lymphocytes, platelets, metastatic cells, and mechanical agents including arterial and venous catheters.

In addition to the homeostatic effects of heparin, arginine through production of nitric oxide provides additional homeostatic control. For example, increased nitric oxide activity inactivates and regulates platelets, leukocytes, macrophage activity, cytokines (thereby reducing macrophage induced lymphocyte activation), smooth muscle contraction, and DNA synthesizing enzymes, etc. Additionally, nitric oxide has cytotoxic effects on virus and other infectious agents. All of which are recognized as potentially injurious to heparin.

It is believed that a mechanism in the promotion of homeostatic control is the regulation of water distribution and its catalytic and hydrolytic effects in a variety of non-homeostatic molecular interactions.

This treatment with its combined effects of heparin and arginine by creating and restoring homeostatic control, plausibly leads to the following:

Prevention of atherosclerosis within blood vessels in states of abnormal and normal lipid environments;

Regression of atherosclerosis;

Prevention of arterial stenosis and re-stenosis following mechanical interventions;

Reduces cardiovascular morbidity and mortality from a variety of causes;

Collateral artery formation which auto-bypasses areas of obstruction or stenosis in vessels affected by atherosclerosis;

Prevention of essential hypertension;

Prevention of secondary forms of hypertension;

Reduction of smooth muscle cell and cardiac muscle cell hypertrophy associated with various forms of hypertension;

Dramatic reduction in thrombogenicity associated with atherosclerosis and numerous other disease states;

Decreased activation of clotting factors;

Decreased rate of thrombosis, and thromboembolism and both macro and microembolic scales;

Decreased activation of platelets, neutrophils, lymphocytes, macrophages, and other whereby blood vessel and tissue injury from ischemia and infarction occur;

Enhanced endogenous and exogenous thrombolysis for restoration of macro and microvascular flow in blood vessels;

Decreased endothelial injury, and injury to other cell types, tissues, and organs, related to infection and cytokines produced by a variety of cellular and disease processes, including immune and inflammatory processes;

Prevention and resolution of HIV infection;

Decreased flow related endothelial cell injury;

Enhanced endothelial regeneration following injury from endogenous processes, disease states, and man-made devices and procedures;

Increases macro and microvascular flow in blood vessels thereby improving oxygenation processes necessary for homeostasis;

Prevention of acute myocardial infarction;

Prevention of cerebrovascular and peripheral vascular ischemic injury and infarction;

Prevention of microembolic myocardial cell dysfunction and disease states;

Minimization of extent of damage to tissues and cells from acute and/or chronic ischemia;

Regulation of growth factor activity for prevention and treatment of hypertrophy in various organs and tissues;

Regulation of lmphocyte and monocyte-macrophage activity for prevention and treatment of immune inflammatory diseases;

Prevention of transplanted tissue rejection;

Treatment and minimization of processes leading to degenerative diseases;

Prevention of congestive heart failure;

Regression and/or functional cure of congestive heart failure;

Regression of neuropathies associated with but not limited to diabetes, amyotrophic lateral sclerosis, multiple sclerosis;

Preservation of renal function in diabetic states and other vasculopathic states;

Minimization of cellular membrane and matrix injury by inactivation of proteolytic and glycolytic enzymes including but not limited to heparinase released by platelets, macrophages, lymphocytes, neutrophils, viruses, bacteria and other infectious agents;

Enhanced cellular and tissue resistance to injury in various disease states;

Enhanced cellular and tissue reparative and generative capacity following injury in various disease states;

Regeneration of gas exchange membranes and blood vessels in lungs resulting in resolution or improvement in gas exchange related to states of chronic emphysema, pulmonary fibrosis, and asthma;

Decreases activation, adhesion, and migration of platelets, neutrophils, lymphocytes, macrophages, and other cell types;

Decreases free radical and re-perfusion injury to cellular components and structures;

Decreased rates of cell transformation to malignant genotype and phenotype; and/or Decreased rate of metastases and viability of metastases in malignant diseases.

Low to high molecular weight heparin preferably having a high degree of sulfation can be used as well as standard heparin as is commercially available. Human, animal and recombinant heparin sources are believed to be useful in practicing the invention and capable of stimulating the full range of responses claimed herein. It is envisioned that the source of exogenous heparin, including the possibility of human recombinant heparin, and the source of arginine imparts no special or additional properties to the homeostatic functionalities observed for the individual elements or their conjoined, synergistic functionalities. Various glycosaminoglycans, similar to heparin, are subject to in vivo epimerization and sulfation resulting from agents which promote acylation reactions and sulfation reactions, such as acetyl salicylic acid, thereby producing heparin or heparin functionality. Thus, for example, heparin sulfate is considered an analog of heparin. Heparin can be used in the form of its salts with physiologically tolerated bases, for example Sodium, Calcium, Magnesium or diethylamine, triethylamine or triethanolamine. Promoters of increased heparin production, such as prostacyclin, are the functional equivalent of heparin, as would be analog's thereof, such as taprostene and may be employed in the present invention.

The regulatory system should benefit from compounds that enhance the activity of prostacyclin, such as defribrotide.

Effective doses of both the heparin and arginine vary with the particular patient condition and the method administration. For example, it is noticed that subcutaneous injection of heparin results in greater concentration in the cellular and membrane domains than by intravenously injection. Effective dosages ranges in the amount from about 2,000 IU to 200,000 IU of heparin daily.

Arginine, as used herein is L-arginine, and is added together with or separately from the heparin. L-arginine also include sulfates thereof and sulfates of their functional analogs. Dosages of arginine are from about 500 mg to 50,000 mg daily.

The physiological condition of the patient will largely dictate the required dosages and frequencies of administration, i.e. weight, age, disease, sex. The compound of the present invention can be formulated for oral, sublingual, subcutaneous, intravenous, transdermed or rectal administrations in dosages and in admixture with pharmaceutical excipients or vehicles including implantation or administered of controlled released devices or vehicles.

For example, the compound of heparin and arginine can be dispersed in a physiological acceptable, non-toxic liquid vehicle, such as water. Alternatively, the compound can be given in tablet, capsule, powder, granules or coated tablet form. The compound can be made in a conventional manner, and may be mixed with conventional pharmaceutical auxiliaries, such as binders, fillers, preservatives, tablet disintegrators, flow regulators, plasticizers, wetting agents, dispersants, emulsifiers, solvents, retarding agents and/or antioxidants. It also can be contained or complexed with lipids in various formulations and molecular arrangements, e.g. lipid tubules.

Essential and secondary forms of hypertension are known to occur from smooth muscle contraction and hypertrophy. Nitric oxide is known to prevent smooth muscle contraction. Therefore, it is believed that the increased nitric oxide produced by the present invention will aid in preventing such contraction and in turn prevent or reverse hypertension, muscle cell hypertrophy, and other states of cellular hypertrophy.

HIV infection is a virus. The virus has been observed to infect every cell type except the endothelial cell which appears to be protected by the highest known level of nitric oxide activity. Certain nitric oxide valence states are known to possess antiviral effects. The increased nitric oxide production coupled with gellular maintenance is expected to be a treatment against the virus and other pathogens. Similar effects are operative against bacteria, fungi, lipopolysaccharides and tumor necrosis factor are bound and inactivated by the heparin-arginine polymers.

Endothelial cell injury and myocardial cell injury occurs from free radicals. Heparin binds super oxide dismutase which absorbs high energy electrons and deactivates free radicals. Heparin and nitric oxide bind free radicals preventing damage to endothelial cells. Additionally, heparin enhances re-endothelial coverage of damaged areas from whatever cause. Similar effects in the extracellular water matrix of all cells is expected to retard and prevent cellular injury and diseases related to free radical formation including atrophic, degenerative, and diseases associated with the aging process.

Congestive heart failure is in part due to free radical injury to myocardial cells. Heparin, super oxide dismutase and nitric oxide all attack and neutralize free radicals, therefore, diseases associated with cellular injury from free radicals are envisioned to be effectively treated and prevented by the present invention. Also, heparin aids in the reconstruction of damaged tissue by complexing and removing extracellular matrix protein accumulations, e.g. fibronectin with consequent reverse of organ hypertrophy states.

Insulinopenic Diabetes is due to damage to the pancreas by lymphocyte mediated processes damaging insulin producing cells in the pancreas. Nitric oxide prevents lymphocyte damage to beta cells of the pancreas responsible for insulin production. Heparin aids cell surface integrity and maintenance. Heparin-arginine coadministration decreases immunologic injury to the pancreas thereby preventing of diabetes. Similar circumstances apply in other tissue types subject to immune injury.

Type II diabetes is due to high insulin levels which damage endothelial cells. Type II diabetes is associated with premature atherosclerosis, hypertension, kidney damage and failure, damage to peripheral nerves, and vascular complications. Obesity leads to excess lipid accumulation which damages endothelial surfaces and accumulation of excess lipids in bilipid layer, further damaging the gel. Continuous release of these substances activates a variety of cells producing the various organ diseases associated with diabetes. Heparin and arginine quiet the system as explained above. Nitric oxide blocks activity of activating factors and various mitogens. Protection of cells by maintenance of gel integrity prevents changes recognized microscopically as disease states in a variety of cell and tissue types.

Emphysema is disruption of endothelial-pneumocyte, alveolar membranes. Free radicals lead to disruption of these cellular gels, damage to bilipid layers, and passage of free radicals through bilipid layers into adjacent endothelial cell and pneumocyte gels. Emphysema is associated with activated platelets, lymphocytes, macrophages and neutrophils in a manner analogous to endothelial cell damage occurring from free radicals. The same mechanisms are operative in the disease of Asthma. By inactivating immune cells and binding cytokines and enzymes the heparin-arginine polymers and gel prevents and treats emphysema, asthma, and pulmonary fibrosis.

Inflammatory disease, as an example, glomerulitis associated with streptococcal infection, involves damage to filtering kidney endothelial cells by antibodies to the strep damaging the heparin-arginine gel with resultant deficiency of nitric oxide production. Nitric oxide deficiency triggers activation of injurious cell types resulting in glomerulitis.

Transforming cells and cancer cells are envisioned to have high levels of DNA replication as a consequence of insufficient nitric oxide generation. Malignant cells contain high levels of desulfated glycosaminoglycans in their extracellular matrix. It is believed that a deficient heparin level accounts for the low sulfation levels observed in these gels. Further, it is believed that uncontrolled heparinase activity may be the proximate cause of low sulfation and malignant transformation and metastatic spread of malignant cells. Inactivation of heparinase, or other functional analogs, heparin prevents transformation to malignant states and metastasis. High nitric oxide levels regulate DNA transcription and oncogene activity to prevent and arrest malignant cells and their progenitors.

Multiple Sclerosis and amyotrophic lateral sclerosis are caused by abnormal immune function damaging neurons. Nitric oxide deactivates lymphocytes and decreases immune damage in these diseases. Heparin binds lymphocyte and macrophage heparinase preventing tissue infiltration by these cells.

In addition, it is recognized that nitric oxide is involved in neural transmission, thus increased nitric oxide enhances neural transmission and effects nerve function and repair. Nitric oxide is recognized to facilitate long term memory in brain cells. Increased nitric oxide production is envisioned to improve long term memory and prevent dementia from a variety of causes.

It is believed that local heparin deficiency leads to uncontrolled, non-homeostatic activity of proteolytic enzymes resulting in a variety of degenerative, scarring, and sclerosing diseases associated with both aging and premature organ dysfunction.

It is believed that local and generalized nitric oxide deficiency leads to diseases associated with abnormal activity of neutrophils, lymphocytes, macrophages, and platelets. Among these are inflammatory diseases, arthritis diseases, and various sclerosing processes and diseases, "normal" aging processes and various degenerative diseases.

Nitric oxide has cytostatic and cytotoxic effect on bacterial and viruses and other infectious agents via ability to inhibit mitochondrial enzyme function in these organisms. It is believed that increased nitric oxide production enhances resistance to infection and can act as an anti-injectious agent. Heparin binds bacterial enzymes and prevents cell and tissue invasion by infectious agents.

It is recognized that heparin, via its association with arginine, enhances regeneration of endothelium following an injury to an endothelial surface. The DNA regulating properties of nitric oxide and the growth factor binding-release properties of heparin undoubtably are involved in this regenerative capacity. By enhancing the heparin-arginine gel properties surrounding and organizing other cell types, it is belived that cell and tissue regeneration in other cell types can also be achieved. It is conceived that such regeneration may occur by functional re-association of damaged cell constituents coincidental with the injury or in a more remote time following the injury.

It will be readily apparent to those skilled in the art that many modifications, derivations and improvements are within the scope of the invention. As such, such modifications, derivations, and improvements should be accorded full scope of protection by the claims appended hereto.

What is claimed is:

1. A method for treating a patient susceptible to or suffering from at least one of atherosclerosis, arteriosclerosis, congestive heart failure, stroke, arterial dysfunction, re-stenosis, hypertension, smooth muscle cell hydrophy, thrombogenicity, clotting disorders, platelet disorders, myocardial infarction, cerebrovascular ischemia, or peripheral vascular ischemia, said method comprising orally administering to said patient a therapeutically effective amount of a first substance selected from the group consisting of heparin, heparin sulfate, taprostene, prostacyclin, and physiologically acceptable salts thereof, and a therapeutically effective amount of a second substance selected from the group consisting of arginine, arginine sulfate, and physiologically acceptable salts thereof.

2. The method of claim 1 wherein said first substance is exogenous heparin.

3. The method of claim 1 wherein said first substance is dispersed in a physiologically acceptable carrier.

4. The method of claim 3 wherein said physiologically acceptable carrier is water.

5. The method of claim 1 wherein said first substance is administered subcutaneously, intravenously, rectally, transdermal or intra pulmonary.

6. The method of claim 1 wherein said second substance is arginine, a functional analog of arginine, a physiological acceptable salt of arginine, or a physiologically acceptable salt of a functional analog of arginine.

7. The method of claim 6 wherein said second substrate is exogenous L-arginine.

8. The method of claim 1 wherein said second substance is dispersed in a physiologically acceptable carrier.

9. The method of claim 8 wherein said physiologically acceptable carrier is water.

10. The method of claim 1 wherein said second substance is administered subcutaneously, intravenously, rectally, transdermally or intra pulmonary.

11. The method of claim 1 wherein said first substance and said second substance are co-administered orally.

12. The method of claim 1 wherein said therapeutically effective amount of the first substance is characterized as containing about 2000 to 200,000 units of heparin, heparin sulfate, taprostene, prostacyclin, or a physiologically acceptable salt thereof.

13. The method of claim 1 wherein said therapeutically effective amount of the second substance comprises about 500 to 50,000 mg arginine, arginine sulfate, or a physiologically acceptable salt thereof.

14. A method of treating cardiovascular disease comprising the step of administering a mixture of arginine and heparin in therapeutic proportions.

15. The method of claim 14, for the treatment of angina pectoris.

16. The method of claim 14, for treatment of cardiovascular systems.

17. The method of claim 14, for oral administration.

* * * * *